United States Patent
Lee et al.

(10) Patent No.: US 7,053,235 B2
(45) Date of Patent: May 30, 2006

(54) (4,5,9,10-TETRAHYDRO-PYREN-2-YL)-CARBAMIC ACID 4-(2-METHYLSULFANYL-ALKYL)-3,5-DINITRO-BENZYL ESTER, METHOD OF SYNTHESIZING THEREOF, AND MOLECULAR ELECTRONIC DEVICE USING THE SAME

(75) Inventors: Hyoyoung Lee, Daejeon (KR); Mun Seok Jeong, Jeollabuk-do (KR); Do Hyun Kim, Daejeon (KR); Taehyoung Zyung, Daejeon (KR)

(73) Assignee: Electronics and Telecommunications Research Institute (KR)

( * ) Notice: Subject to any disclaimer, the term of this patent is extended or adjusted under 35 U.S.C. 154(b) by 18 days.

(21) Appl. No.: 10/864,065

(22) Filed: Jun. 8, 2004

(65) Prior Publication Data

US 2005/0012092 A1    Jan. 20, 2005

(30) Foreign Application Priority Data

Jul. 16, 2003    (KR)    .................. 10-2003-0048664

(51) Int. Cl.
*C07C 271/12*    (2006.01)

(52) U.S. Cl. ................. 560/27; 560/28; 257/40; 326/100

(58) Field of Classification Search .................. 560/27, 560/28; 257/40; 326/100
See application file for complete search history.

(56) References Cited

U.S. PATENT DOCUMENTS

| | | | | |
|---|---|---|---|---|
| 3,950,407 A | * | 4/1976 | Hammar | ..................... 562/405 |
| 4,568,684 A | * | 2/1986 | Rentzea et al. | ............. 514/383 |
| 6,348,700 B1 | | 2/2002 | Ellenbogen et al. | |

OTHER PUBLICATIONS

Krzeminski et al, J. Phys. Chem. B. 2001, vol. 105, 6321-6323.*

"Molecular rectification with M/(D-o-A LB film)/M junctions" A. Brady, et al., J. Mater. Chem., 1999 9, pp. 2271-2275.

* cited by examiner

*Primary Examiner*—Shailendra Kumar
(74) *Attorney, Agent, or Firm*—Blakely Sokoloff Taylor & Zafman (57) ABSTRACT

A new compound derivative that can be used to form a unit molecular film as a rectifier in a molecular electronic device, a new rectifying compound (4,5,9,10-tetrahydro-pyren-2-yl)-carbamic acid 4-(2-methylsulfanyl-alkyl)-3,5-dinitrobenzyl ester and its derivative (4,5,9,10-Tetrahydro-pyren-2-yl)-carbamic acid 4-(2-methylsulfanyl-alkyl)-3,5-dinitrobenzyl ester, and methods of synthesizing the compounds are provided.

2 Claims, 6 Drawing Sheets

| A | B | C |
|---|---|---|
| 0 | 0 | 0 |
| 1 | 0 | 0 |
| 0 | 1 | 0 |
| 1 | 1 | 1 |

| A | B | C |
|---|---|---|
| 0 | 0 | 0 |
| 1 | 0 | 1 |
| 0 | 1 | 1 |
| 1 | 1 | 1 |

(4,5,9,10-TETRAHYDRO-PYREN-2-YL)-CARBAMIC ACID 4-(2-METHYLSULFANYL-ALKYL)-3,5-DINITRO-BENZYL ESTER, METHOD OF SYNTHESIZING THEREOF, AND MOLECULAR ELECTRONIC DEVICE USING THE SAME

BACKGROUND OF THE INVENTION

This application claims the priority of Korean Patent Application No. 2003-48664 filed on Jul. 16, 2003, in the Korean Intellectual Property Office, the disclosure of which is incorporated herein in its entirety by reference.

1. Field of the Invention

The present invention relates to a compound derivative, in which an electron acceptor and an electron donor are coupled, and more particularly, to a compound derivative of carbamate, a method of synthesizing the same, and a molecular device using the same.

2. Description of the Related Art

A molecular electronic or a molecular optical device that has been currently reported is mainly in the form of an electronic device, has a basic structure of two metal electrodes and an organic molecular layer disposed between two metal electrodes. The organic molecule is configured to have a characteristic of organic semiconductor between the molecule two metal electrodes. In this case, the dimension of the organic molecule is in a range of a few nano meters.

Generally, the structure of the molecular device is determined from the disposition method of the organic molecule between the two electrodes, however, the structure can broadly be divided into two structures, i.e., a horizontal and a vertical structure. The horizontal structure has a configuration that an organic compound is disposed between the two metal electrodes placed on a same plane. That is, after forming a gap having nano distance between the two electrodes according to an existing semiconductor manufacturing process, the organic compound is disposed in the gap. While, the vertical structure is formed that a lower electrode is first formed, and an organic compound is placed on the lower electrode, and then an upper electrode is placed on the organic compound.

Until the present time, the organic molecular device material required for the development of the molecular electronic device has been sought out, focusing mainly on the functional purposes, such as a characteristic of molecular wire, a molecular switch, and a molecular rectifier. These technical fields have been studied mostly in advanced countries including U.S.A and Europe as the development of nano technology.

The development history of the molecular rectifying device has the same chronicle as the development of the molecular electronic device. The necessity of development of a molecular device was first proposed through a desire to develop a device utilizing the diode characteristic, i.e., an organic semiconductor characteristic of a molecular rectifying material. Aviram and Ratner of IBM in 1974 introduced a method of formation of a device having a molecular diode rectifying characteristic using a unit molecular characteristic.

According to Aviram and Ratner, when an electron donor (D) and an electron acceptor (A) in a molecule exist in the form of a sigma bond which acts as a spacer, a polarization will occur in the molecule with one directional polarization. After the polarized molecules are arranged in one direction, that is, when forming an electron donor-spacer-electron acceptor structure, a metal electrode on each side is connected, and current will flow in one direction.

This hypothesis was proven by Mattern and his co-workers in 1999 through a partial experiment. They reported that a rectifying characteristic was realized from the experiment carried out by forming an organic LB (Langmuir film) between two electrodes. Also, Metzger group found that the rectifying characteristic can be realized in $\pi$-bond instead of $\sigma$-bond. Professor M. A. Reed et al. in Yale University have reported that a rectifying diode characteristic can be generated by using an electric potential difference between two metals, such as gold and titanium, in an asymmetric organic compound which has no electron donor-spacer-electron acceptor.

Despite of efforts to develop a rectifying diode device using an organic molecular characteristic, a clear and direct proof regarding the rectifying characteristic of the molecular electronic device, as to whether it is generated from the organic molecular characteristic has not been disclosed yet. Up to the present time, the question of the rectifying characteristic of the molecular device using an organic molecule can not be explained whether it comes from the sole characteristic of the organic compound or it is a phenomenon occurred between the two metals including the organic molecule.

Accordingly, there is a strong desire to develop a new molecular rectifying material that can explicate the rectifying characteristic of molecular electronic device. However, the development of a molecular rectifying material is very difficult. Particularly, a synthetic difficultness of an organic compound is considered as a big hindrance for developing a molecular rectifying material.

For example, when an electron donor and an electron acceptor are co-existed in a reactor, a precipitation, generally in the form of a salt, will occur due to a charge transfer between the two molecules. For this reason, synthesizing a covalent compound having an electron donor-sigma bond-electron acceptor required for forming the molecular electron rectifying material is practically difficult.

SUMMARY OF THE INVENTION

The present invention provides a new donor-sigma-acceptor compound derivative obtained through a coupling reaction between (4-sulfanyl-alkyl)-3,5-dinitro-benzyl alcohol as an electron acceptor and 2-aminopyrene as an electron donor.

The present invention also provides a method of synthesizing the compound derivative.

The present invention also provides a molecular electronic device using the compound derivative.

According to an aspect of the present invention, there is provided that a compound performing as a molecular rectifying action having the following chemical formula.

[Formula I]

[Formula 1]

where R represents hydrogen, a methyl radical, an alkyl radical, or an acetyl radical, and n can be an integer between 1 and 25. Particularly, there is provided a compound that R is an acetyl radical, and n is 1.

According to another aspect of the present invention, it is provided that a molecular diode device composed of a first electrode, a second electrode opposite side of the first electrode, and molecular film formed by combining a compound having above chemical formula with the second electrode on a surface of the second electrode.

Also, according to another aspect of the present invention, there is provided a molecular logic circuit device which is a logic gate formed by arranging molecular diode device as unit device, wherein the molecular diode device is composed of a first electrode, a second electrode opposite side of the first electrode, and molecular film formed by combining a compound having above chemical formula with the second electrode on a surface of the second electrode.

According to another aspect of the present invention, there is provided a method of synthesizing a compound comprising preparing 4,5,9,10-tetrahydro-pyren-2-yl-amine, preparing 4-acetylsulfanyl methyl-3,5-dinitro-benzyl chloroformate, and obtaining a compound having above chemical formula by a coupling reaction between 4,5,9,10-tetrahydro-pyren-2-yl-amine and 4-acetylsulfanyl methyl-3,5-dinitro-benzyl chloroformate, and wherein the compound performs molecular rectifying action.

Here, the preparing the 4,5,9,10-tetrahydro-pyren-2-yl-amine comprises synthesizing 2-nitro-4,5,9,10-tetrahydro-pyrene by reacting tetrahydro-pyrene with nitric acid, and synthesizing the 4,5,9,10-tetrahydro-pyren-2-yl-amine by reducing the 2-nitro-4,5,9,10-tetrahydro-pyrene.

At this time, the reduction reaction uses tin chloride ($SnCl_2$) as a catalyst.

Also, preparing the 4-acetylsulfanyl methyl-3,5-dinitro-benzyl chloroformate comprises preparing thioacetic acid 4-hydroxymethyl-2,6-dinitro-benzyl ester, and synthesizing 4-acetylsulfanyl methyl-3,5-dinitro-benzyl chloroformate by reacting thioacetic acid 4-hydroxymethyl-2,6-dinitro-benzyl ester with trichlorophosgene.

An action to activate the 4,5,9,10-tetrahydro-pyren-2-yl-amine can further be performed using a basic catalyst before a coupling reaction. At this time, the basic catalyst can be triethylamine as a third amine radical.

The coupling reaction can be performed using a pyridine group catalyst. The pyridine group catalyst is dimethylaminopyridine.

A method of manufacturing a molecular electronic device including forming a molecular film on a surface of the first electrode between the compound having above chemical formula and a surface of the first electrode and forming a second electrode on the molecular film, and a characteristic of molecular device are reported.

According to the present invention, there is provided a new compound, i.e., (4,5,9,10-Tetrahydro-pyren-2-yl)-carbamic acid 4-(2-methylsulfanyl-alkyl)-3,5-dinitro-benzyl ester that can be used as a rectifying material in a molecular electronic device.

DETAILED DESCRIPTION OF THE INVENTION

Hereinafter, the present invention will be described more fully with reference to the accompanying drawings in which preferred embodiment of the invention are shown. This invention may, however be embodied in many different forms and should not be construed as being limited to the embodiments set forth herein, rather, these embodiments are provided so that this disclosure is thorough and complete, and fully conveys the concept of the invention to those skilled in the art. In the drawings, the thickness of layers and regions are exaggerated for clarity. To facilitate understanding, identical reference numerals have been used, where possible, to designate identical elements that are common to the figures.

In an embodiment of the present invention, tetrahydro-pyrene is used as an electron donor, and a new compound having a thiol radical ($S^-$) in a particular location in the tetrahydro-pyrene is provided. Also, a method of manufacturing the new compound is provided. In this case, 4-alkyl-sufanyl-alkyl-3,5-dinitro-benzyl-alcohol or 3,5-dinitro-benzyl-alcohol is used as a electron acceptor.

Figure 1:
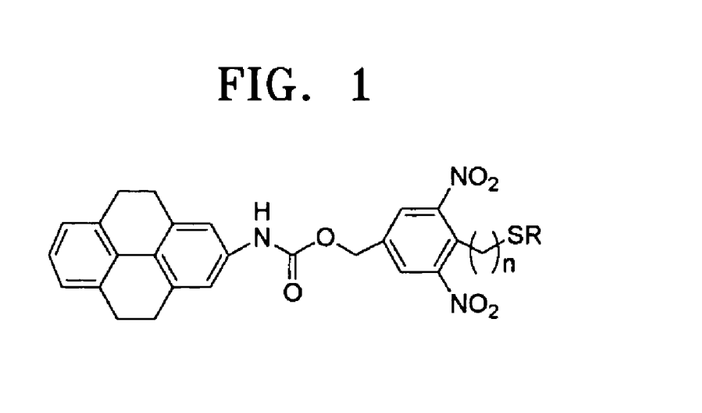
FIG. 1 shows a chemical formula of (4,5,9,10-Tetrahydro-pyren-2-yl)-carbamic acid 4-(2-methylsulfanyl-alkyl)-3,5-dinitro-benzyl ester, a compound derivative according to an embodiment of the present invention.

A new compound derivative having a basic configuration of donor-sigma-bonding-acceptor-SR as depicted in FIG. 1 as a result of coupling reaction of the electron donor with the electron acceptor and a method of manufacturing is provided.

FIG. 1 is a chemical formula of (4,5,9,10-Tetrahydro-pyren-2-yl)-carbamic acid 4-(2-methylsulfanyl-alkyl)-3,5-dinitro-benzyl ester.

Referring to FIG. 1, R represents hydrogen, an alkyl radical, or an acetyl radical, and n represents an integer between 1 and 25.

A compound derivative having a configuration of Donor-sigma-bonding-Acceptor-SR as depicted in FIG. 1 according to an embodiment of the present invention can be used as an electron donor-acceptor organic material for a new molecular electronic device having a molecular rectifying characteristic.

Also, by utilizing a conducting probe-atomic force-microscopy (CP-AFM) or a scanning tunneling microscopy (STM), a measurement of current-voltage between two electrodes and a direction of current flow may be performed. Particularly, the organic material is applicable to synthesize a vertical or a horizontal type molecular electronic device having a rectifying characteristic. Also, such rectifying material can be applied to a molecular electron array device and a logic circuit using the molecular electron array.

In order to apply the compound derivative having chemical formula depicted in FIG. 1 to a molecular device, fixing the compound derivative to an electrode of the molecular electronic device is required. Therefore, in the embodiment of the present invention, a method of fixing the compound derivative to the electrode of molecular electronic device, and a method of manufacturing a unit molecular device using the method of fixing the compound derivative to the electrode and characteristics of molecular device will be described.

First, an example of synthesizing a compound derivative according to the present invention having a basic configuration as depicted in FIG. 1 will be described referring to a reaction depicted in FIG. 2.

Synthesis Method

Figure 2:
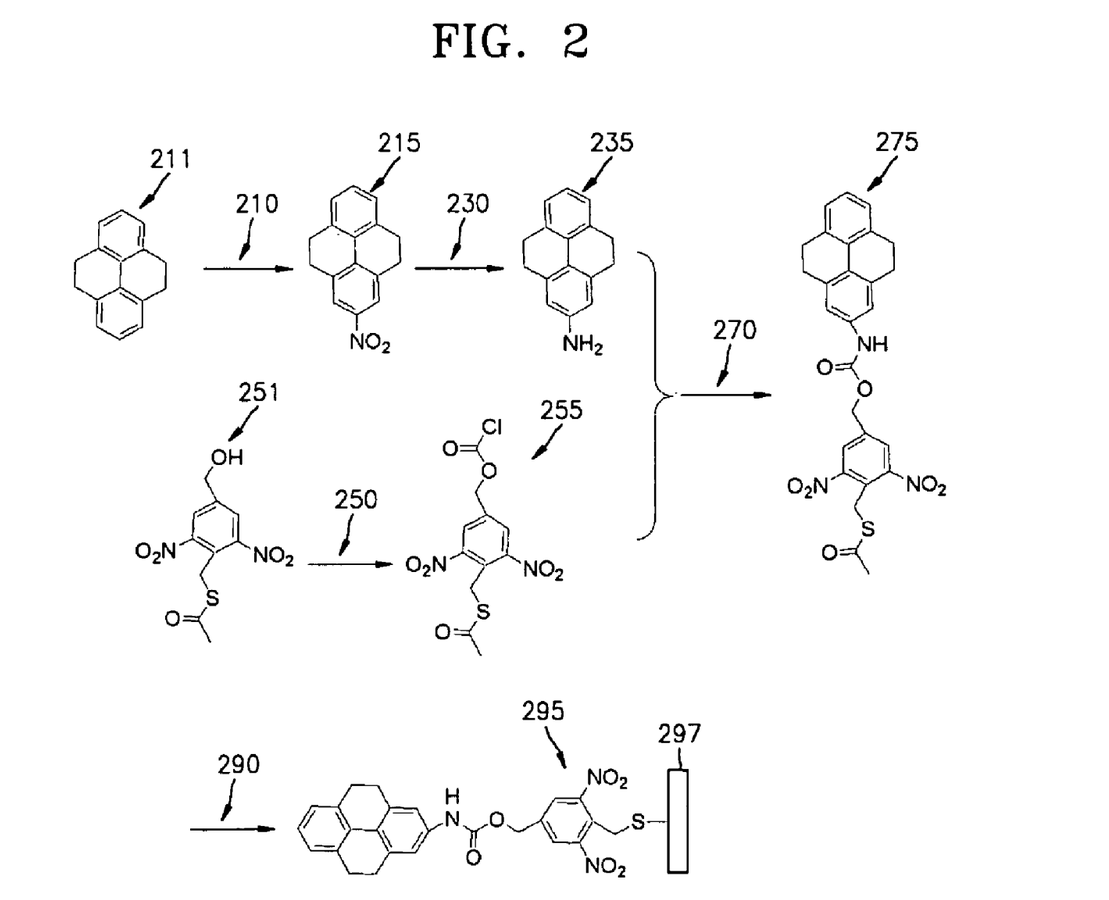
FIG. 2 shows reactions for forming (4,5,9,10-Tetrahydro-pyren-2-yl)-carbamic acid 4-(2-methylsulfanyl-alkyl)-3,5-dinitro-benzyl ester according to an embodiment of the present invention.

FIG. 2 shows a reaction formula for describing the method of synthesizing (4,5,9,10-Tetrahydro-pyren-2-yl)-carbamic acid 4-(2-methylsulfanyl-alkyl)-3,5-dinitro-benzyl ester according to an embodiment of the present invention.

Referring to the reaction formula depicted in FIG. 2, the method of synthesizing (4,5,9,10-Tetrahydro-pyren-2-yl)-carbamic acid 4-(2-methylsulfanyl-alkyl)-3,5-dinitro-benzyl ester according to the chemical formula of FIG. 1 and the fixation method of the (4,5,9,10-Tetrahydro-pyren-2-yl)-carbamic acid 4-(2-methylsulfanyl-alkyl)-3,5-dinitro-benzyl ester to the electrode of the molecular electronic device comprise the following steps.

That is, a first step 210 for synthesizing 2-nitro-4,5,9,10-tetrahydro-pyrene 215 from tetrahydro-pyrene 211 reaction with nitric acid, and a second step 230 for synthesizing 4,5,9,10-tetrahydro-pyren-2-yl-amine 235 from a reaction between 2-nitro-4,5,9,10-tetrahydro-pyrene 215 and $SnCl_2$ which is a reduction agent.

Also, the steps can include a third step 250 for synthesizing 4-acetylsulfanyl methyl-3,5-dinitro-benzyl chloroformate 255 from a reaction between thioacetic acid 4-hydroxymethyl-2,6-dinitro-benzyl ester 251 and trichlorophosgene.

Also, the steps can further include a fourth step 270 for synthesizing thioacetic acid 2,6-dinitro-4-(4,5,9,10-tetrahydro-2-ylcarbamoyloxy methyl)-benzyl ester 275 from a reaction between 4,5,9,10-tetrahydro-pyren-2-yl-amine 235 and 4-acetylsulfanyl methyl-3,5-dinitro-benzyl chloroformate 255.

The above steps can further include a fifth step 290 for forming a thin film 295 using the obtained material, i.e., thioacetic acid 2,6-dinitro-4-(4,5,9,10-tetrahydro-2-ylcarbamoyloxy methyl)-benzyl ester 275 as the molecular electronic device.

First step (210 in FIG. 2)

At the first step 210 in FIG. 2, the compound 2-nitro-4,5,9,10-tetrahydro-pyrene 215 can be synthesized from the compound tetrahydro-pyrene 211 by a nucleophilic reaction. That is, the electron rich location 2 or 7 of the tetrahydro-pyrene 211 attacks the electron deficient intermediate location of the nitro compound.

More specifically, after dissolving the 4,5,9,10-tetrahydro-pyrene 211 in glacial acetic acid, by reacting the solution with fuming nitric acid, the 2-nitro-4,5,9,10-tetrahydro-pyrene 215 was synthesized according to the first step 210. The first step 210 reaction is performed at temperature of 0~30° C., preferably at 15~20° C. for 5~10 minutes with stirring enough to have complete mixing. Concentration of nitric acid can be 2~3M per 1 mole of 4,5,9,10-tetrahydro-pyrene 211, preferably 2.5M. A solvent can be any solvent that does not affect the reaction, but preferably acetic acid or dichloromethane.

Second Step (230 in FIG. 2)

At the second step 230 in FIG. 2, tin chloride ($SnCl_2$) as a reduction agent can be used for the reaction when the 2-nitro-4,5,9,10-tetrahydro-pyrene 215 is reduced to 4,5,9,10-tetrahydro-pyren-2-yl-amine 235, for higher yield.

More specifically, the 4,5,9,10-tetrahydro-pyren-2-yl-amine 235 is synthesized by substituting a nitro radical of the 2-nitro-4,5,9,10-tetrahydro-pyrene 215 to amine radical using tin chloride ($SnCl_2$), i.e., a reduction agent. Methods for substituting the nitro radical to the amine radical can include a method using a metal catalyst like Raney nickel Ni, but an activation of Raney nickel cannot be easily achieved. Therefore, in the embodiment of the present invention, tin chloride is used as the catalyst.

Solvent can be an organic solvent that does not affect the reaction 230, preferably acetylacetate anhydride or ethanol anhydride. Aqueous solution of 15~25 equivalent sodium ethylene diamine tetraacetic acid (sodium EDTA), preferably 18~20 equivalent sodium EDTA can be added to the solution to remove excessive tin used for the reaction after reaction.

Third Step (250 in FIG. 2)

At the second step 250 in FIG. 2, 4-acetylsulfanyl methyl-3,5-dinitro-benzyl chloroformate 255 can be obtained through a reaction between thioacetic acid 4-hydroxymethyl-2,6-dinitro-benzyl ester 251 and trichlorophosgene compound.

More specifically, in order to synthesize chioroformate radical using hydroxy radical of the thioacetic acid 4-hydroxymethyl-2,6-dinitro-benzyl ester 251, trichlorophosgene is used. In a conventional method for synthesizing the chioroformate radical, a liquefied phosgene gas was used, but in the embodiment of the present invention, a much safer method of synthesizing the chioroformate radical using trichlorophosgene is introduced.

Preferably, one equivalent trichlorophosgene is used to thioacetic acid 4-hydroxymethyl-2,6-dinitro-benzyl ester 251. Preferably, the reaction catalyst is one equivalent of a weak salt of pyridine group. The reaction condition has to be an anhydride condition, accordingly, anhydrous dichloromethane is suitable for the solvent.

Preferably, the reaction time is for 5~7 hours. Preferably, the reaction temperature is 0° C. maintained in an ice bath, and more preferably, the temperature is maintained at 0° C. throughout the reaction including when adding and after adding the pyridine and the trichlorophosgene.

Fourth Step (270 in FIG. 2)

As the same manner as the third step reaction in FIG. 2, in order to obtain thioacetic acid 2,6-dinitro-4-(4,5,9,10-tetrahydro-2-ylcarbamoyloxy methyl)-benzyl ester 275, the synthesized 4,5,9,10-tetrahydro-pyren-2-yl-amine 235 and the 4-acetylsulfanyl methyl-3,5-dinitro-benzyl chloroformate 255 are coupled under a basic catalyst.

Reaction solvent can be an anhydride solvent, and more preferably, an anhydrous dichloromethane. Catalyst that can be used to activate the 4,5,9,10-tetrahydro-pyren-2-yl-amine 235 is a third amine group, more preferably, 0.9~1.0 equivalent of triethylamine.

Preferably, after dissolving the 4,5,9,10-tetrahydro-pyren-2-yl-amine 235 and the triethylamine in the dichloromethane solvent, the solution is mixed for 10~20 minutes. Afterward, the 4-acetylsulfanyl methyl-3,5-dinitro-benzyl chloroformate 255 is added to the solution and preferably the solution is mixed for approximately an hour with stirring. A pyridine group catalyst, preferably 0.9~1.0 equivalent of dimethyl aminopyridine can be added to the solution. Preferably, reaction time is 20~24 hours, more preferably, 24 hours.

As the reaction progresses, white solid precipitation occurs. The white solid precipitation can be separated by filtering. Preferably, contaminants are removed by washing the white solid several time using a solvent like dichloromethane that does not dissolve the white solid, more preferably, re-crystallization can be performed using a solvent like ester group in which the white solid dissolves. Particularly, it is preferable to try to re-crystallize the white solid after dissolving it to tetrahydrofurane by adding hexane.

Fifth Step (290 in FIG. 2)

Finally, in order to fix the organic molecule 275 synthesized from the fourth step 270 on the molecular electronic device electrode, a self assembling method is used. That is, a self assembled molecular layer (SAM) 295, i.e., 4,5,9,10-tetrahydro-pyren-2-yl-carbamic acid 4-mercaptomethyl-3,5-dinitro-benzyl ester is formed on the gold electrode 287 by dipping the gold electrode substrate 297 having a molecular device on its surface in a solution containing thioacetic acid 2,6-dinitro-4-(4,5,9,10-tetrahydro-2-ylcarbamoyloxy methyl)-benzyl ester 275 with an acidic or a basic catalyst, or without an acidic or a basic catalyst.

Preferably, the solution can be an organic solution having a high solubility in which the thioacetic acid 2,6-dinitro-4-(4,5,9,10-tetrahydro-2-ylcarbamoyloxy methyl)-benzyl ester 275 synthesized in the fourth step is dissolved.

Preferable the organic solvent can be alcohol, tetrahydrofurane (THF), or dimethyl formamide (DMF), more preferably, oxygen free and anhydrous solvent prepared using a freeze-pump-thaw method. When forming a self assembled molecular layer, a temperature is maintained in a range of 0~80° C. under oxygen free and anhydrous atmosphere. The molecular device is dipped in the solution conventionally for 24~48 hours. Afterward, it is washed by pouring a solvent on the surface of the molecular device. At this time, the solvent for washing the molecular device can be alcohol, THF, or distilled water, more preferably, it is washed first with alcohol or THF and then it is washed with distilled water.

Sixth Step (295 in FIG. 2)

As the same manner as described above, a self assembled molecular film 295 on a surface of the gold 297 electrode to be used to a molecular device can be fabricated.

Figure 6A:
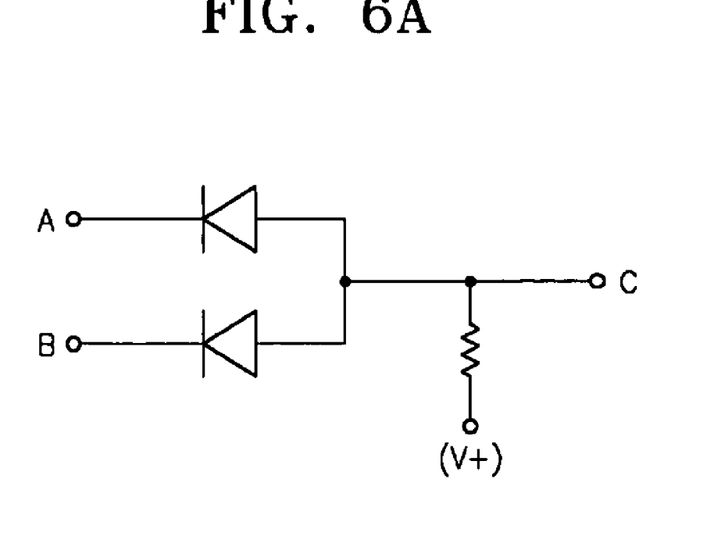
FIGS. 6A and 6B are schematic diagrams of circuit and operation of an AND gate to be formed by molecular device according to an embodiment of the present invention.

Seventh Step (FIG. 6)

A molecular device composed of metal/molecular film/metal can be manufactured by depositing an upper electrode on the molecular film device.

An effectiveness of the method of synthesizing according to the embodiment of the present invention is proved through actual experiments.

[Experiments]

Synthesis of 2-nitro-4,5,9,10-tetrahydro-pyrene 215 in FIG. 2

A water bath that can maintain reactants and a reactor temperature at 20° C. is prepared. 3.1g (15mmol) of tetrahydro-pyrene 211 was poured in a two-circle rounded bottom flask having a magnetic stirrer placed in the water bath, and the reactant was dissolved adding 200 ml of glacial acetic acid. 13.5 ml of fuming acid was slowly added to the solution extending over 5 minutes while stirring the solution. After mixing the reactants for 5 more minutes, the solution was quenched by adding 100 ml of ice water, then yellow solids were formed. The solution containing yellow solid was further stirred for approximately one hour. After filtering the solution, the obtained yellow solids were washed with cold water. The yellow solids were dissolved in dichloromethane solvent. Afterward, 3.56 g (14.2 mmol) of a light yellow solid, i.e., 2-nitro-4,5,9,10-tetrahydro-pyrene 215 was obtained by purifying the solution passing through a silica gel chromatography column using 10% acetylactate and a hexane group solvent. In this case, yield was 94.3%.

The structure of the product was examined using a hydrogen nuclear magnetic resonance (NMR), and found that it matched the structure of compound numeral 215 depicted in FIG. 2. The hydrogen NMR obtained was [$^1$H NMR (400 MHz, $CDCl_3$) (ppm): 7.98 (2H, s), 7.26 (1H, dd), 7.16 (2H, t), 2.97 (8H, m); MS: m/z (%) 189 (10), 202 (15), 221 ($M^+$, 100)]

Synthesis of 4,5,9,10-tetrahydro-pyren-2-yl-amine 235 in FIG. 2

An oil bath that can maintain reactants and a reactor temperature at 100° C. with a thermometer is prepared. A 100 ml of two-circle rounded bottom flask (hereinafter, flask) having a condenser and a stirrer is placed in the oil bath. 1.0 g (3.98 mmol) of 2-nitro4,5,9,10-tetrahydro-pyrene 215 and 4.48 g (19.0 mmol) of tin chloride ($SnCl_2$) were poured into the flask. After dissolving the reactants in 25 ml of anhydrous acetylactate in the flask, it was reacted for 12 hours with stirring.

After cooling the reactant, 20 equivalents of sodium EDTA solution was added to the solution to remove unreacted excessive tin. White solid precipitations were removed by filtering. A product was extracted by adding ethyl ether to the filtrate, and the solution was concentrated by removing the ethyl ether under reduced pressure. 0.85 g (3.83 mmol) of yellow solid, i.e., 4,5,9,10-tetrahydro-pyren-2-yl-amine 235 was obtained purifying through a silica gel chromatography column. In this case, yield was 96%.

The structure of the product was examined using a hydrogen nuclear magnetic resonance (NMR), and found that it matched the structure of compound numeral 235 depicted in FIG. 2. The hydrogen NMR obtained was [$^1$H NMR (400 MHz, $CDCl_3$) (ppm): 7.08 (3H, s), 6.46 (2H, s), 3.5 (2H, brs), 2.85 (8H, m). MS: m/z (%) 189 (20), 202 (35), 251 ($M^+$, 100)]

Synthesis of 4-acetylsulfanyl methyl-3,5-dinitro-benzyl Chloroformate 255 in FIG. 2

In a water bath that can maintain reactants and a reactor temperature at 0° C. with a thermometer, a 100 ml of one-circle rounded bottom flask (flask) having a stirrer is placed. 3 ml of dichloromethane anhydride, 0.19 g (0.66 mmol) of thioacetic acid 4-hydroxymethyl-2,6-dinitro-benzyl ester 251, and 0.053 ml (0.66 mmol) of pyridine were mixed in the flask. After stirring the mixture for approximately 10 minutes at temperature maintained of 0° C., 0.136 g (0.66 mmol) of trichlorophosgene was added to the mixture and stirred for 6 hours.

The mixture reactants were poured into a distilled water containing ice, and stirred for approximately 10 minutes. After extracting ethyl ether, the solution was concentrated by removing the ethyl ether. Consequentially, 0.22 g (0.63 mmol) of white solid, i.e., 4-acetylsulfanyl methyl-3,5-dinitro-benzyl chloroformate 255 was obtained purifying through a silica gel chromatography column. In this case, yield was 95%.

The structure of the product was examined using a hydrogen nuclear magnetic resonance (NMR), and found that it matched the structure of compound numeral 255 depicted in FIG. 2. The hydrogen NMR obtained was [$^1$H NMR (400 MHz, CDCl$_3$) (ppm): 8.13 (2H, s), 5.42 (2H, s), 4.62 (2H, s), 2.26 (3H, S)]

Synthesis of Thioacetic Acid 2,6-dinitro-4-(4,5,9,10-tetrahydro-2-ylcarbamoyloxy methyl)-benzyl Ester 275 in FIG. 2

In a water bath that can maintain reactants and a reactor temperature at 25° C. with a thermometer, a 100 ml of one-circle rounded bottom flask (flask) having a stirrer is placed. 20 ml of dichloromethane anhydride, 0.093 g (0.42 mmol) of 4,5,9,10-tetrahydro-pyren-2-yl-amine 235, and 0.058 ml (0.4 mmol) triethylamine were mixed in the flask. After stirring the mixture for 10 minutes, 0.23 g (0.66 mmol) of 4-acetylsulfanyl methyl-3,5-dinitro-benzyl chloroformate 255 was added slowly. After stirring the mixture reactants for approximately 1 hour, 0.049 g (0.4 mmol) of dimethylaminopyridine was added, and mixed for approximately 24 hours.

White solid precipitations were produced as the reaction progresses. After collecting the white solid precipitations by filtering, the white solid precipitations were dissolved in tetrahydrofurane to try re-crystallization. As the result of re-crystallization which was performed by adding hexane to the solution, 0.20 g of white solid was obtained. In this case, yield was 95%.

The structure of the product was examined using a hydrogen nuclear magnetic resonance (NMR), and found that it matched the structure of compound numeral 275 depicted in FIG. 2. The hydrogen NMR obtained was [$^1$H NMR (400 MHz, DMSO-d$_6$) (ppm): 9.90 (s,1H), 8.37 (s, 2H), 7.22 (s, 2H), 7.07 (s, 3H), 5.31 (s, 2H), 4.50 (s, 2H), 2.78 (s, 8H), 2.30 (s, 3H). $^{13}$C NMR (400 MHz, DMSO-d$_6$) (ppm): 194.7, 153.3, 150.7, 140.3, 138.1, 136.1, 134.6, 130.3, 128.0, 126.9, 126.3, 125.4, 116.4, 116.0, 63.9, 30.2, 28.1, 25.6, 25.2.]

Formation of Molecular Electronic Device Thin Film 295 in FIG. 2

A self assembling method was used to fix the obtained compound in the previous step 275 in FIG. 2 to a nanopore molecular electronic device electrode. In a glove box maintaining oxygen free and anhydrous condition, 20 ml of bial, 2.67 mg (0.005 mmol) of thioacetic acid 2,6-dinitro-4-(4,5, 9,10-tetrahydro-2-ylcarbamoyloxy methyl)-benzyl ester are dissolved in a solvent, which is treated to be oxygen free using a freeze-pump-thaw method, at room temperature and stirred for 5 minutes. A nanopore molecular device in which a lower electrode is formed of gold was immersed in the above solution for 24 hours. After taking the nanopore molecular device out of the solution, it was sequentially washed with alcohol, ethanol, and distilled water.

The formation of self assembling molecular film 297 (in FIG. 2) on a surface of the gold electrode can be proved by quartz crystal microbalance (QCM) data in which oscillation is reduced due to the adherence of organic molecules on the surface of the gold electrode as time passes.

Figure 3:
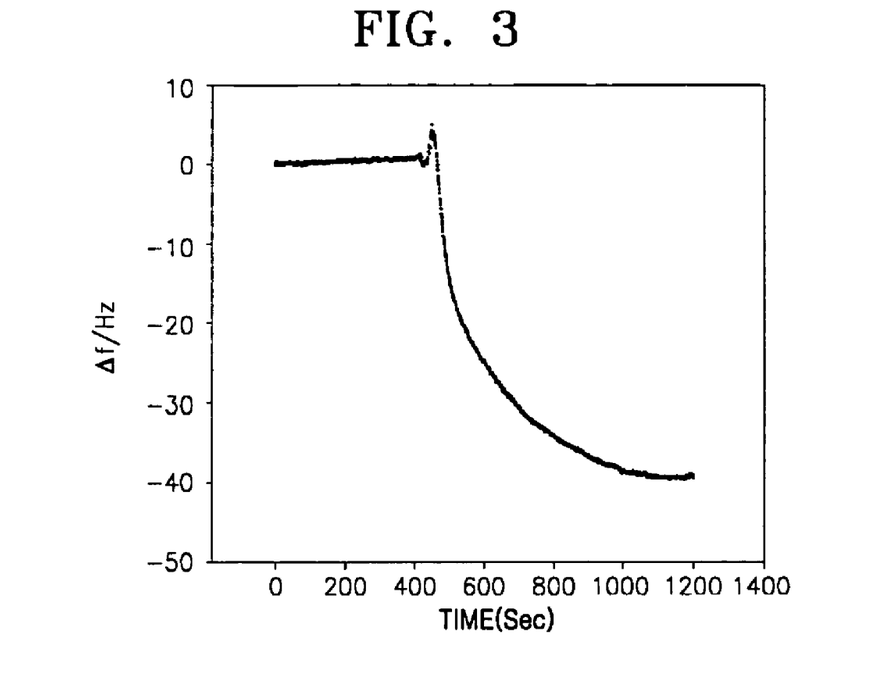
FIG. 3 is a Quartz Crystal Microbalance (QCM) data graph for proving a formation of self assembling molecular film of molecular electronic device on a surface of gold electrode according to an embodiment of the present invention.

FIG. 3 is a QCM data graph for proving existence of self assembling molecular film formed on a surface of a gold electrode. Referring to FIG. 3, the QCM data shows that unit molecular films are saturated on the surface of the gold electrode at approximately 1,200 second after commencing the formation of the self assembling molecular film. The saturation state in FIG. 3 was obtained when a concentration of compound 275 dissolved in DMF was approximately $9.188 \times 10^{-11}$ mol. The compound derivative synthesized in this manner according to an embodiment of the present invention has a thiol radical at the end portion of the molecular electron acceptor, thereby effectively forming self assembling molecular films on a surface of a metal electrode.

Manufacturing a Molecular Electronic Device (FIG. 6) and an Embodiment of Diode Device Characteristic A molecular device having a gold electrode, a surface of which has self assembling molecular films was dried in a low temperature vacuum oven (40° C., $10^{-3}$ Torr) for more than 2 hours. The molecular device was attached to a deposition equipment which is maintained pressure at 10-6 Torr and temperature at −78° C. By depositing an upper electrode on the molecular device, a formation of a molecular electronic device having a self assembling molecular film between two electrodes was achieved.

Figure 4A:
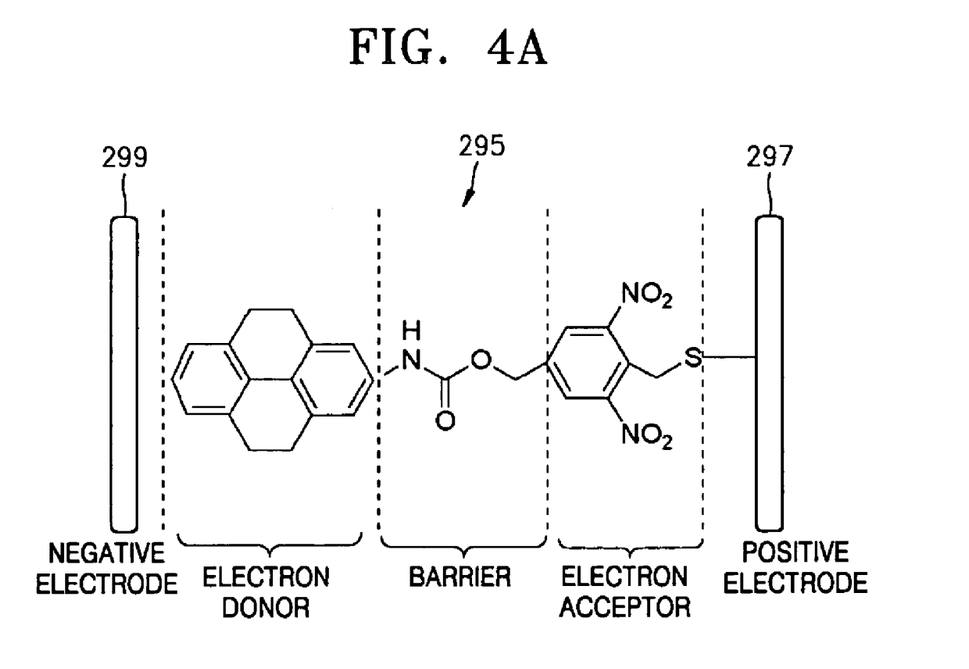
FIG. 4A is a schematic diagram of an unit molecular diode device to which a compound derivative is applied according to the present invention.
Figure 4B:
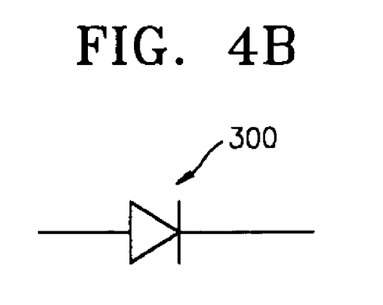
FIG. 4B is a circuit diagram of an unit molecular diode device to which a compound derivative is applied according to the present invention.
Figure 4C:
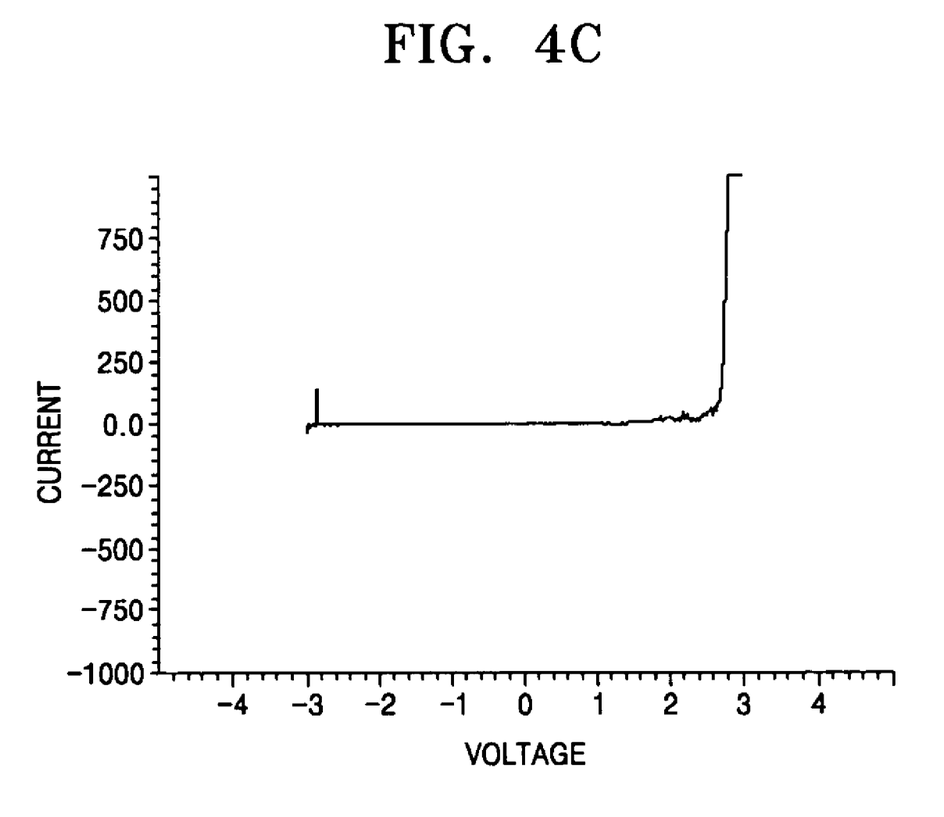
FIG. 4C is a graph showing a current-voltage characteristic of a unit molecular diode device depicted in FIG. 4A.

FIGS. 4A and 4B are schematic drawings for describing an operation principle of a molecular diode device to which the compound according to the embodiment of the present invention is applied. FIG. 4C is a graph showing a current-voltage characteristic of a unit molecular diode device.

Referring to FIG. 4A, as mentioned earlier, a self assembling molecular film 295 from the compound numeral 275 in FIG. 2 is formed on a surface of the gold electrode, i.e., a first electrode 297. At this time, the compound constituting the self assembling molecular film 295 acts as an electron donor-spacer-electron acceptor as depicted in FIG. 4A. When a second electrode, i.e., a negative electrode facing the first electrode, i.e., a positive electrode, is formed by a method described earlier like a deposition method, a molecular diode device capable of operating as the diode circuit 300 depicted in FIG. 4B is formed.

Measurements of current vs. voltage showing a rectifying characteristic of the molecular diode device is shown in FIG. 4C.

Figure 5:
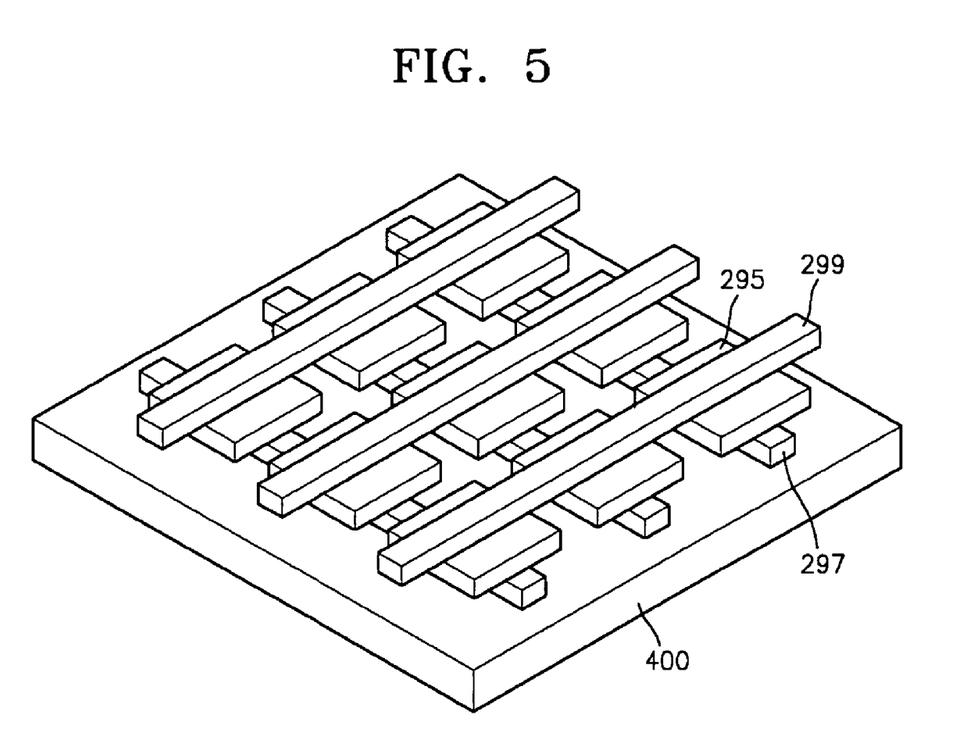
FIG. 5 is a perspective view of diode device arrayed in 3×3 rows according to the present invention.

The molecular diode device can be configured in many different arrays in a molecular device. FIG. 5 is a schematic drawing of molecular diode devices arranged in an array of 3×3.

Referring to FIG. 5, a plurality of patterned and parted lower electrodes 297 are formed of a metal like gold on a substrate 400. Self assembling molecular films 295 by self bonding are formed on the lower electrodes 297 using the compound according to the embodiment of the present invention. The self assembling molecular films 295 can be patterned unit device by unit device using a variety of patterning methods like selective exposure of the lower electrode 297. After forming unit devices of self assembling molecular film 295, respectively, on the lower electrode 297, a plurality of patterned upper electrode 299 are formed on the self assembling molecular films 295.

In this manner, a molecular device in which an array of molecular diode devices is formed as a unit device on a substrate 400 can be formed.

While, the molecular device can be configured to an AND gate or an OR gate by arranging the molecular diode devices in an array of 2×2.

Figure 6B:
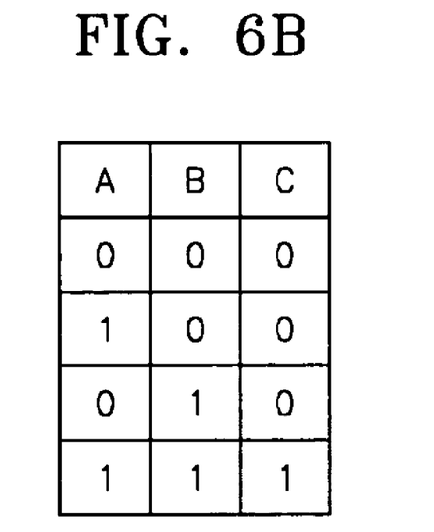

FIGS. 6A and 6B are schematic drawings of an AND gate circuit to be composed of molecular devices and operation of the same.

Referring to FIGS. 6A and 6B, the molecular diode device configured as in FIG. 4 according to the embodiment of the present invention can be configured to an AND gate by arranging in an array of 2×2 as shown in FIG. 6A. In this case, the overall array device can operate as shown in FIG. 6B.

Figure 7A:
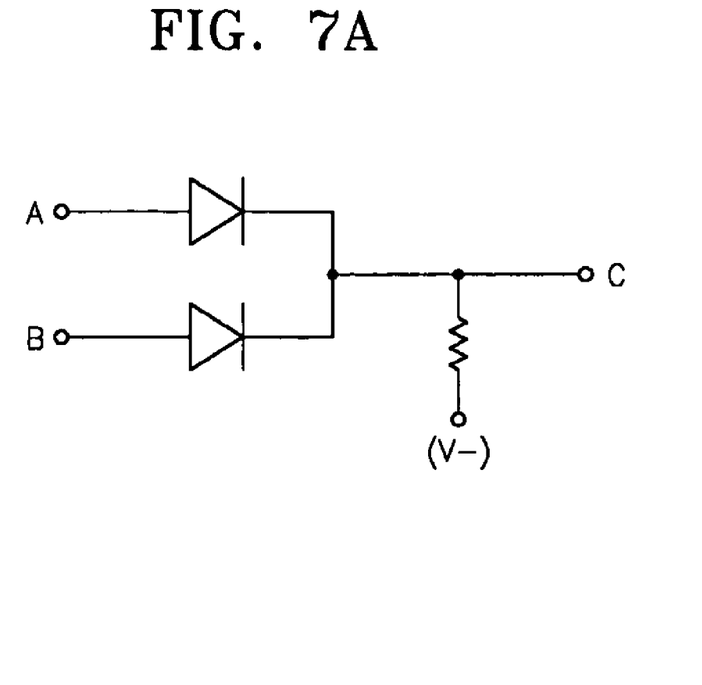
FIGS. 7A and 7B are schematic diagrams of circuit and operation of an OR gate to be formed by molecular devicesaccording to an embodiment of the present invention.
Figure 7B:
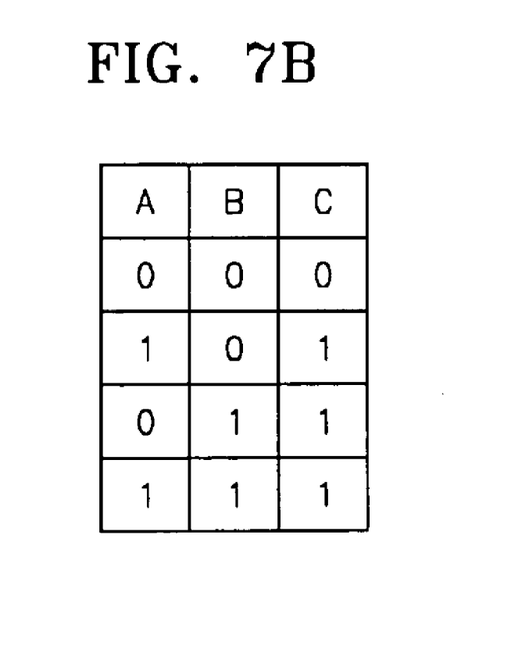

FIGS. 7A and 7B are schematic drawings of an OR gate circuit to be composed of molecular device and operation of the same.

Referring to FIGS. 7A and 7B, the molecular diode device configured as in FIG. 4 according to the embodiment of the present invention can be configured to an OR gate by arranging in an array of 2×2 as shown in FIG. 7A. In this case, the overall array device can operate as shown in FIG. 7B.

The compound according to the embodiment of the present invention can be used as a material for realizing a rectifying characteristic or a switching characteristic by introducing to a molecular device. The molecular device composed of the compound according to the embodiment of the present invention can be structured to a logic circuit device such as OR, XOR, or AND.

According to the detailed description of the present invention, there is provided a new compound, i.e., 4,5,9,10-tetrahydro-pyren-2-yl-carbamic acid 4-mercaptomethyl-3,5-dinitro-benzyl ester that can realize a rectifying characteristic by disposing between two metal electrodes. Also, it is provided a method of synthesizing the compound.

The compound according to the present invention can be used as an electron donor-acceptor organic material in a new molecular electronic device having a molecular rectifying characteristic. Particularly, a horizontal or a vertical type of molecular electronic device having a rectifying characteristic or an arrayed device of the compound can be manufactured by using the above organic material.

Also, the compound according to the present invention can effectively form a self assembling molecular film on a surface of a metal electrode such as gold electrode by means of combining between the metal electrode and an end portion of the compound. That is, the formation of the self assembling molecular film on the surface of the gold electrode is possible because of the thiol radical which is an end portion of the compound according to the present invention.

Accordingly, a molecular electronic device can be structured by placing an upper electrode on the self assembling molecular film formed on the surface of the metal electrode by which combined with the new synthesized compound.

A fundamental characteristic, i.e., the rectifying characteristic of the device can be measured by measuring the current-voltage and direction of current flow between the two electrodes. Such characteristics can be directly measured on the surface of the self assembling molecular film by using a conducting probe atomic force microscopy (CP-AFM) or a scanning tunneling microscopy (STM). While this invention has been particularly shown and described a portion of the compound synthesized according to the embodiments of the present invention, it will be understood by those skilled in the art that various changes in form and details may be made therein without departing from the sprit and scope of the invention as defined by the appended claims.

What is claimed is:

1. A compound having a following chemical formula that performs molecular rectifying:

where R represents one of hydrogen H, methyl radical, alkyl radical, and acetyl radical, and n represents an integer between 1 and 25.

2. The compound of claim 1, wherein R is acetyl radical, and n is one.

* * * * *